United States Patent
Clark et al.

(10) Patent No.: US 6,995,295 B2
(45) Date of Patent: Feb. 7, 2006

(54) ALKYLAROMATICS PRODUCTION

(75) Inventors: Michael C. Clark, Seabrook, TX (US); Ronald Joseph Cimini, Friendswood, TX (US); Charles M. Smith, Houston, TX (US); Brian Maerz, Chelmsford, MA (US)

(73) Assignees: ExxonMobil Chemical Patents Inc., Houston, TX (US); Washington Group International, Boise, ID (US)

( * ) Notice: Subject to any disclaimer, the term of this patent is extended or adjusted under 35 U.S.C. 154(b) by 388 days.

(21) Appl. No.: 10/252,767

(22) Filed: Sep. 23, 2002

(65) Prior Publication Data

US 2004/0059167 A1 Mar. 25, 2004

(51) Int. Cl.
C07C 2/68 (2006.01)

(52) U.S. Cl. .................. 585/449; 585/467
(58) Field of Classification Search ........ 585/449, 585/467
See application file for complete search history.

(56) References Cited

U.S. PATENT DOCUMENTS

| | | | |
|---|---|---|---|
| 3,293,192 A | 12/1966 | Maher et al. ............. 252/430 |
| 3,308,069 A | 3/1967 | Wadlinger et al. ........ 252/455 |
| 3,442,795 A | 5/1969 | Kerr et al. ............... 208/120 |
| 3,449,070 A | 6/1969 | McDaniel et al. ......... 23/111 |
| 3,494,971 A * | 2/1970 | Fenske ...................... 585/449 |
| 3,702,886 A | 11/1972 | Argauer et al. ........... 423/328 |
| 3,709,979 A | 1/1973 | Chu .......................... 423/328 |
| 3,751,504 A | 8/1973 | Keown et al. ............. 260/672 |
| 3,751,506 A | 8/1973 | Burress .................. 260/671 R |
| 3,755,483 A | 8/1973 | Burress .................. 260/671 R |
| 3,766,093 A | 10/1973 | Chu ....................... 252/455 Z |
| 3,832,449 A | 8/1974 | Rosinski et al. .......... 423/328 |

(Continued)

FOREIGN PATENT DOCUMENTS

| | | |
|---|---|---|
| EP | 0293032 | 7/1993 |
| EP | 0 323 663 | 9/1994 |
| EP | 0629549 | 12/1994 |
| EP | 0432814 | 9/1995 |
| EP | 0 467 007 | 4/1996 |
| EP | 0 485 683 | 1/2001 |
| FR | 2 706 888 | 12/1994 |
| WO | 97/17290 | 5/1997 |
| WO | WO 98/07673 | 2/1998 |
| WO | WO 99/65601 | 12/1999 |
| WO | 01/21562 | 3/2001 |

OTHER PUBLICATIONS

Abstract, CN 1 051 166, "Process for Making Ethyl Benzene by Reacting Dilute Ethylene with Benzene", China Petrochem. Cor., XP 002275731, (May 8, 1991).

(Continued)

Primary Examiner—Thuan D Dang
(74) Attorney, Agent, or Firm—D. M. Tyus; L. A. Kubena

(57) ABSTRACT

A process is described for producing an alkylaromatic compound by reacting an alkylatable aromatic compound with a feed comprising an alkene and an alkane in a multistage reaction system comprising at least first and second series-connected alkylation reaction zones each containing an alkylation catalyst. At least the first alkylation reaction zone is operated under conditions of temperature and pressure effective to cause alkylation of the aromatic compound with the alkene in the presence of the alkylation catalyst, the temperature and pressure being such that the aromatic compound is partly in the vapor phase and partly in the liquid phase. An effluent comprising the alkylaromatic compound, unreacted alkylatable aromatic compound, any unreacted alkene and the alkane is withdrawn from the first alkylation reaction zone and at least part of the alkane is removed from the effluent to produce an alkane-depleted effluent. The alkane-depleted effluent is then supplied to the second alkylation reaction zone.

19 Claims, 1 Drawing Sheet

U.S. PATENT DOCUMENTS

| | | |
|---|---|---|
| RE28,341 E | 2/1975 | Wadlinger et al. ........... 208/120 |
| 3,894,104 A | 7/1975 | Chang et al. ........... 260/668 R |
| 3,923,636 A | 12/1975 | Mead et al. ................... 208/58 |
| 3,972,983 A | 8/1976 | Ciric .......................... 423/328 |
| 4,016,218 A | 4/1977 | Haag et al. ............. 260/671 R |
| 4,076,842 A | 2/1978 | Plank et al. ................ 423/328 |
| 4,107,224 A | 8/1978 | Dwyer ................... 260/671 R |
| RE29,948 E | 3/1979 | Dwyer et al. ............... 208/110 |
| 4,234,231 A | 11/1980 | Yan ................................ 299/4 |
| 4,439,409 A | 3/1984 | Puppe et al. ................ 423/328 |
| 4,556,477 A | 12/1985 | Dwyer ....................... 208/111 |
| 4,891,458 A | 1/1990 | Innes et al. ................. 585/323 |
| 4,992,606 A | 2/1991 | Kushnerick et al. ........ 585/467 |
| 5,073,653 A | 12/1991 | Butler ......................... 585/449 |
| 5,077,445 A | 12/1991 | Le .............................. 585/467 |
| 5,149,894 A | 9/1992 | Holtermann et al. ........ 585/467 |
| 5,236,575 A | 8/1993 | Bennett et al. ............... 208/46 |
| 5,250,277 A | 10/1993 | Kresge et al. ........... 423/329.1 |
| 5,258,565 A | 11/1993 | Kresge et al. .............. 585/467 |
| 5,292,698 A | 3/1994 | Chu et al. ..................... 502/84 |
| 5,300,722 A | 4/1994 | Steigelmann et al. ....... 585/467 |
| 5,362,697 A | 11/1994 | Fung et al. .................... 502/71 |
| 5,371,310 A | 12/1994 | Bennett et al. .............. 585/467 |
| 5,430,211 A | 7/1995 | Pogue et al. ................ 585/323 |
| 5,453,554 A | 9/1995 | Cheng et al. ............... 585/467 |
| 5,476,978 A | 12/1995 | Smith, Jr. et al. ........... 585/323 |
| 5,491,277 A | 2/1996 | Stine et al. .................. 585/719 |
| 5,493,065 A | 2/1996 | Cheng et al. ............... 585/467 |
| 5,557,024 A | 9/1996 | Cheng et al. ............... 585/467 |
| 5,600,048 A | 2/1997 | Cheng et al. ............... 585/449 |
| 5,856,607 A | 1/1999 | Kim ........................... 585/448 |
| 5,880,320 A | 3/1999 | Netzer ........................ 585/448 |
| 6,077,498 A | 6/2000 | Diaz Cabañas et al. .... 423/702 |
| 6,252,126 B1 | 6/2001 | Netzer ........................ 585/446 |

OTHER PUBLICATIONS

Abstract, FR 2 706 888, "Method for alkylating aromatics, especially for preparation of ethylbenzene or cumene", (Dec. 30, 1994).

* cited by examiner

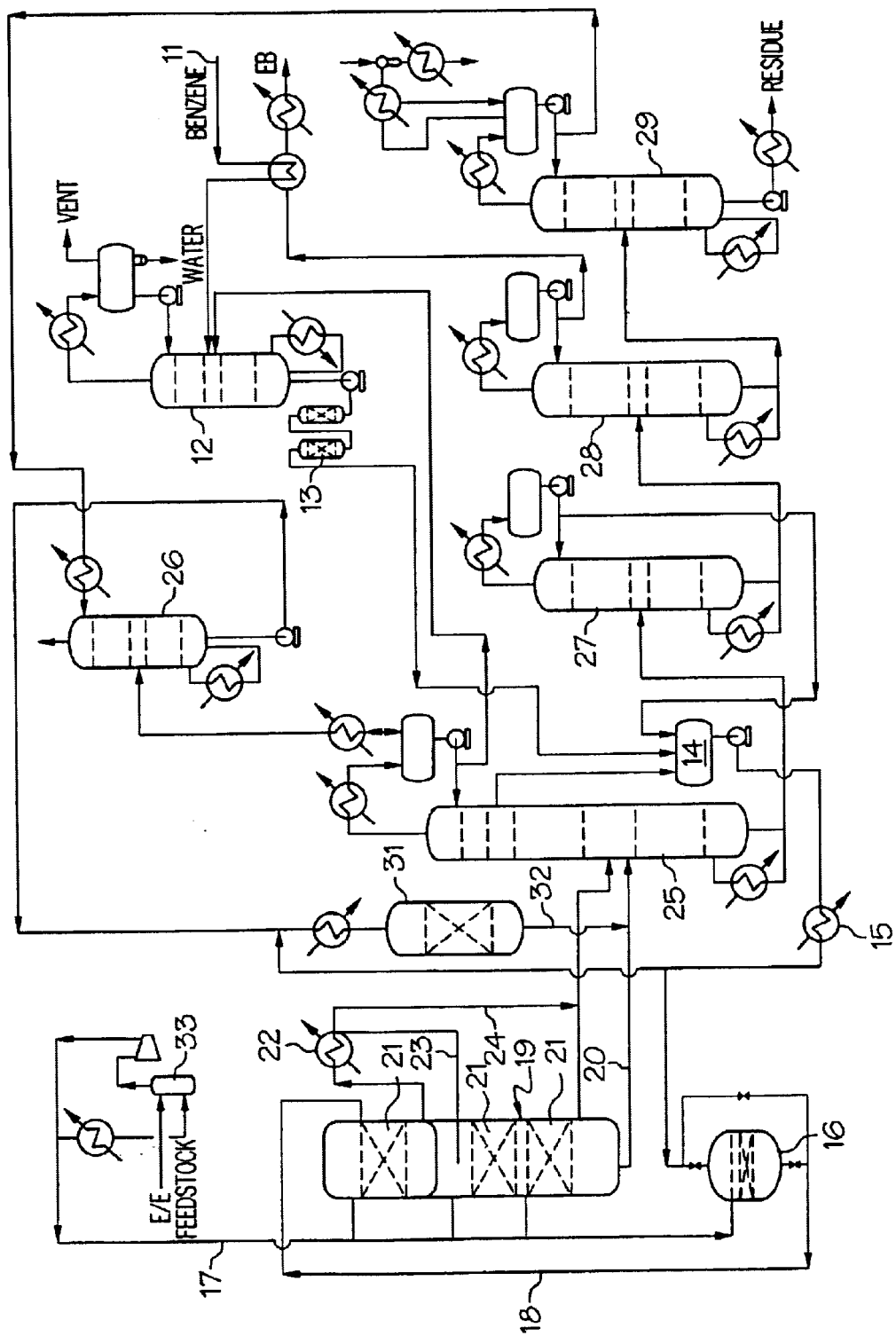

ALKYLAROMATICS PRODUCTION

FIELD

The present invention relates to a process for producing alkylaromatic compounds, particularly ethylbenzene.

BACKGROUND

Ethylbenzene is a key raw material in the production of styrene and is produced by the reaction of ethylene and benzene in the presence of an acid catalyst. Old ethylbenzene production plants, typically built before 1980, used $AlCl_3$ or $BF_3$ as the acidic catalyst. Newer plants have in general been switching to zeolite-based acidic catalysts.

Commercial ethylbenzene manufacturing processes typically require the use of polymer grade ethylene, which has a purity exceeding 99.9 mol %. However, the purification of ethylene streams to polymer grade is a costly process and hence there is considerable interest in developing processes that can operate with lower grade ethylene streams. One such ethylene source is the dilute ethylene obtained as an off gas from the fluid catalytic cracking or steam cracking unit of a petroleum refinery which, after removal of reactive impurities, such as propylene, typically contains about 20–80 wt % ethylene, with the remainder being ethane together with minor amounts of hydrogen, methane and benzene.

Three types of ethylation reactor systems are used for producing ethylbenzene, namely, vapor phase reactor systems, liquid phase reactor systems, and mixed phase reactor systems.

In vapor-phase reactor systems, the ethylation reaction of benzene and ethylene is carried out at a temperature of about 380–420° C. and a pressure of 9–15 kg/cm$^2$-g in multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions, the formation of xylene isomers as trace products occurs by side reactions. This xylene formation in vapor phase processes can yield an ethylbenzene product with about 0.05–0.20 wt % of xylenes. The xylenes show up as an impurity in the subsequent styrene product, and are generally considered undesirable.

In order to minimize the formation of PEBs, a stoichiometric excess of benzene, about 400–900% per pass, is applied, depending on process optimization. The effluent from the ethylation reactor contains about 70–85 wt % of unreacted benzene, about 12–20 wt % of ethylbenzene product and about 3–4 wt % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. Nos. 3,751,504 (Keown et al.), 3,751,506 (Burress), and 3,755,483 (Burress).

In most cases, vapor phase ethylation systems use polymer grade ethylene feeds. Moreover, although commercial vapor phase processes employing dilute ethylene feeds have been built and are currently in operation, the investment costs associated with these processes is high and the products contain high concentrations of xylene impurities.

In recent years the trend in industry has been to shift away from vapor phase reactors to liquid phase reactors. Liquid phase reactors operate at a temperature of about 220–270° C., which is under the critical temperature of benzene (290° C.). One advantage of the liquid phase reactor is the very low formation of xylenes and oligomers. The rate of the ethylation reaction is lower compared with the vapor phase, but the lower design temperature of the liquid phase reaction usually economically compensates for the negatives associated with the higher catalyst volume. Thus, due to the kinetics of the lower ethylation temperatures, resulting from the liquid phase catalyst, the rate of the chain reactions forming PEBs is considerably lower; namely, about 5–8% of the ethylbenzene is converted to PEBs in liquid phase reactions versus the 15–20% converted in vapor phase reactions. Hence the stoichiometric excess of benzene in liquid phase systems is typically 150–400%, compared with 400–800% in vapor phase.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in these alkylation/transalkylation reactions, see, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos. WO97/17290 and WO01/21562 (ITQ-2).

Commerical liquid phase ethylbenzene plants normally employ polymer grade ethylene. Moreover, although plants can be designed to accept ethylene streams containing up to 30 mol % ethane by increasing the operating pressure, the costs associated with the design and operation of these plants are significant.

Technology has also been developed for the production of ethylbenzene in a mixed phase using reactive distillation. Such a process is described in U.S. Pat. No. 5,476,978. Mixed phase processes can be used with dilute ethylene streams since the reaction temperature of the ethylation reactor is below the dew point of the dilute ethylene/benzene mixture, but well above the bubble point. The diluents of the ethylene feed, ethane, methane and hydrogen, remain essentially in the vapor phase. The benzene in the reactor is split between vapor phase and liquid phase, and the ethylbenzene and PEB reaction products remain essentially in the liquid phase. However, reactive distillation units are complex and expensive and the catalyst is prone to deactivation as a result of the production of ethylene oligomers.

U.S. Pat. No. 6,252,126 discloses a mixed phase process for producing ethylbenzene by reaction of a dilute ethylene stream containing 3 to 50 mol % ethylene with a benzene stream containing 75 to 100 wt % benzene. The reaction is conducted in an isothermal ethylation section of a reactor vessel which also includes a benzene stripping section, where the unreacted benzene is thermally stripped from the ethylation products. Integrated, countercurrent vapor and liquid traffic is maintained between the ethylation section and the benzene stripping section.

SUMMARY

The present invention resides in a process for producing an alkylaromatic compound by reacting an alkylatable aromatic compound with a feed comprising an alkene and an alkane in a multistage reaction system comprising a plurality of series-connected alkylation reaction zones each containing an alkylation catalyst, the process comprising the steps of:

(a) operating at least one of said alkylation reaction zones under conditions of temperature and pressure effective to cause alkylation of said aromatic compound with said alkene in the presence of said alkylation catalyst, said temperature and pressure being such that part of said aromatic compound is in the vapor phase and part is in the liquid phase;

(b) withdrawing from said one alkylation reaction zone an effluent comprising said alkylaromatic compound, unreacted alkylatable aromatic compound, any unreacted alkene and said alkane;

(c) removing at least part of said alkane from said one alkylation reaction zone effluent to produce an alkane-depleted effluent; and (d) supplying said alkane-depleted effluent to another of said alkylation reaction zones.

Typically, the feed comprises at least 20 wt % of said alkene, such as from 20 to 80 wt % of said alkene. Typically, said alkane has the same number of carbon atoms as said alkene.

In one emodiment, said alkylatable aromatic compound includes benzene, said alkene includes ethylene and said alkane includes ethane.

In said one embodiment, said conditions in step (a) include a temperature of 150 to 270° C. and a pressure of 675 to 8300 kPa Conveniently, said alkylation catalyst is selected from MCM-22, PSH-3, SSZ-25, ERB-1, ITQ-1, ITQ-2, MCM-36, MCM-49, MCM-56, faujasite, mordenite and zeolite beta.

DESCRIPTION OF THE DRAWINGS

The accompanying drawing is a flow diagram of a process for producing ethylbenzene in accordance with one example of the invention.

DETAILED DESCRIPTION OF THE EMBODIMENTS

The present invention provides a mixed phase process for producing alkylaromatic compounds from a dilute alkene feedstock, in which the feedstock also includes an alkane and typically other impurities. Although the process is particularly directed to the production of ethylbezene from dilute ethylene, it is equally applicable to the production of other $C_2$–$C_6$ alkylaromatic compounds, such as cumene, as well as $C_6$+ alkylaromatics, such as $C_8$–$C_{16}$ linear alkylbenzenes. Where the feedstock is dilute ethylene, the impurities present will normally include ethane, methane and/or hydrogen.

The process involves reacting an alkylatable aromatic compound with the dilute alkene feedstock in a multistage alkylation reaction system comprising at least first and second, and normally at least three, series-connected alkylation reaction zones, which each contain an alkylation catalyst and which are typically located in a single reaction vessel. At least the first alkylation reaction zone, and normally each alkylation reaction zone, is operated under conditions of temperature and pressure effective to cause alkylation of the aromatic compound with the alkene in the presence of the alkylation catalyst, the temperature and pressure being such that the aromatic compound is partly in the vapor phase and partly in the liquid phase.

The effluent from the first alkylation reaction zone comprises the desired alkylaromatic compound, unreacted alkylatable aromatic compound, any unreacted alkene (alkene conversion is expected to be 98–99.99%) and the alkane impurity. Before being fed to the second alkylation reaction zone, the first alkylation reaction zone effluent is passed to a separation system including, for example, a flash drum where at least part of the alkane impurity is removed. The alkane-depleted effluent is then fed to the second alkylation reaction zone where additional dilute alkene feedstock is added for reaction with the unreacted aromatic compound. Removing the alkane impurity between the first and second alkylation reaction zones increases the liquid to vapor ratio and hence the alkene conversion in the second alkylation reaction zone. Where the process employs more than two alkylation reaction zones, the effluent from each zone is fed to the separation system prior to passage to the next zone or to the transalkylation unit. Alternatively, the effluent from every second bed or every third bed, etc., can be fed to the separation system depending on the economics and optimization of a specific plant.

In addition to, and upstream of, the series-connected alkylation reaction zones, the alkylation reaction system may also include a by passable reactive guard bed that may be bypassed, which is normally located in a prereactor separate from the remainder of the alkylation system. The reactive guard bed is also loaded with alkylation catalyst, which may be the same of different from the catalyst used in the multi-stage alkylation reaction system, and is maintained under ambient or up to alkylation conditions. The alkylatable aromatic compound and the dilute alkene feedstock are passed through the reactive guard bed prior to entry into the first zone of the series-connected alkylation reaction zones. The reactive guard bed not only serves to effect the desired alkylation reaction but is also used to remove any reactive impurities in the feeds, such as nitrogen compounds, which could otherwise poison the remainder of the alkylation catalyst. The catalyst in the guard bed is therefore subject to more frequent regeneration and/or replacement than the remainder of the alkylatioin catalyst and hence the guard bed is normally provided with a by-pass circuit so that the alkylation feedstocks can be fed directly to the series-connected alkylation reaction zones when the guard bed is out of service. The reactive guard bed may operate in all liquid phase or mixed phase in co-current upflow or downflow operation.

The multi-stage alkylation reaction system used in the process of the invention is normally operated so as to achieve essentially complete conversion of the alkene in the dilute alkene feedstock. However, for some applications, it may be desirable to operate at below 100% alkene conversion and employ a separate finishing reactor downstream of the multi-stage alkylation reaction system (not shown). The finishing reactor would also contain alkylation catalyst, which could be the same of different from the catalyst used in the multi-stage alkylation reaction system and could be operated under, vapor phase, liquid phase or mixed phase alkylation conditions.

The multi-stage alkylation reaction system used in the process of the invention is highly selective to the desired monoalkylated product, such as ethylbenzene, but normally produces at least some polyalkylated species. Thus the effluent from the final alkylation stage, after passage through the alkane separation system and recovery of the monoalkylated product, is fed to a transalkylation reactor, which is normally separate from the alkylation reactor, where additional monoalkylated product is produced by reacting the polyalkylated species with additional aromatic compound.

Reactants

The reactants used in the process of the invention include an alkylatable aromatic compound and a dilute alkene alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agent useful in the process of this invention includes a dilute alkene feed which contains at least one alkane and typically at least one alkane having the same number of carbon atoms as the alkene. For example, where the alkene is ethylene, the alkane may be ethane. Typically, the dilute alkene feed comprises at least 20 wt % of the alkene, such as from 20 to 80 wt % of the alkene. One particularly useful feed is the dilute ethylene stream obtained as an off gas from the fluid catalytic cracking unit of a petroleum refinery Preferably, the reactants in the process of the invention are benzene and dilute ethylene and the desired reaction product is ethylbenzene.

Alkylation and Transalkylation Catalysts

The alkylation and transalkylation catalyst used in the process of the invention is not critical but normally comprises a molecular sieve selected from MCM-22, PSH-3, SSZ-25, ERB-1, ITQ-1, ITQ-2, MCM-36, MCM-49 and MCM-56.

MCM-22 and its use to catalyze the synthesis of alkylaromatics, including ethylbenzene, is described in U.S. Pat. Nos. 4,992,606; 5,077,445; and 5,334,795. PSH-3 is described in U.S. Pat. No. 4,439,409. SSZ-25 and its use in aromatics alkylation are described in U.S. Pat. No. 5,149,894. ERB-1 is described in European Patent No.0293032. ITQ-1 is described in U.S. Pat. No. 6,077,498. ITQ-2 is described in International Patent Publication No. WO97/17290 and WO01/21562. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S. Pat. No. 5,236,575. The use of MCM-49 to catalyze the synthesis of alkylaromatics, including ethylbenzene, is described in U.S. Pat. Nos. 5,493,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554. The entire contents of all the above patent specifications are incorporated herein by reference.

Alternatively, the alkylation and transalkylation catalyst can comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

As a further alternative, the alkylation and transalkylation catalyst can comprise a large pore molecular sieve having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The above molecular sieves may be used as the alkylation or transalkylation catalyst in the process of the invention without any binder or matrix, i.e., in so-called self-bound form. Alternatively, the molecular sive may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The same catalyst may be used in both the transalkylation zone and the alkylation zones of the present process. Preferably, however, different catalysts are chosen for the two zones, so as to be tailored for the particular reactions catalyzed therein. For example, in one embodiment, MCM-22, either in bound or unbound form, is used in the reactive guard bed and the series-connected alkylation reaction zones and a suitable transalkylation is used in the transalkylation zone. In such an embodiment, any finishing reactor could include MCM-22 for liquid phase operation or ZSM-5 for vapor phase operation.

Reaction Conditions

In the process of the invention, the alkylation reaction in at least the first, and normally in each, of the series-connected alkylation reaction zones takes place under mixed liquid/vapor phase conditions, such that the alkylatable aromatic compound is partly in the vapor phase and partly in the liquid phase.

Particular conditions for carrying out the mixed phase alkylation of benzene with ethylene may include a temperature of from about 150 to 270° C., a pressure of about 675 to about 8300 kPa; such as a temperature from about 170 to 220° C. and pressure of about 1500 to 4000 kPa, a WHSV based on ethylene of from about 0.1 to about 10 hr$^{-1}$, and a mole ratio of benzene to ethylene from about 1 to about 10.

Where the alkylation system includes a reactive guard bed, this may be operated under liquid phase conditions or vapor phase conditions or mixed liquid/vapor phase conditions, but is preferably operated under liquid phase conditions. The guard bed will preferably operate at a temperature between 20 and 270° C. and a pressure between about 675 to about 8300 kPa.

The transalkylation reaction may also take place under liquid phase conditions or vapor phase conditions or mixed liquid/vapor phase conditions, but preferably takes polace under liquid phase conditions. Particular conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 100 hr$^{-1}$ and a mole ratio of benzene to polyethylbenzene of from 1:1 to 30:1.

One embodiment of the process of the invention, in which the alkylatable aromatic compound is benzene and the alkylating agent is a dilute ethylene stream, is shown in the accompanying drawing.

Referring to the drawing, in the embodiment shown a benzene feed 11 is passed to a drying column 12, where the water content of the benzene is preferably reduced to below 20 ppm. From the column 11, the benzene is passed to a reservoir 14 by way of treaters 13 which serve to remove catalyst poisons, particularly nitrogen and sulfur containing organic species from the benzene. From the reservoir 14, the benzene is pumped to a heat exchanger 15, where the benzene is indirectly heated by high pressure steam, before being fed to a reactive guard bed 16.

The reactive guard bed 16 also receives a dilute ethylene feed 17 from a compressor 18 (which may or may not be present) such that the benzene and dilute ethylene pass cocurrently down through a bed of alkylation catalyst in the guard bed. Alternately, the flow can be co-current upflow. The guard bed 16 typically operates at or near to 100% ethylene conversion but may operate at lower conversions (alternately, no ethylene can be introduced to the guard bed) so that the effluent 18 leaving the guard bed is composed of ethylbenzenes, unreacted benzene and unreactive light impurites (mainly ethane) from the dilute ethylene feed. The guard bed effluent 18 is then passed to the top bed in a main alkylation reactor 19, which includes a plurality of vertically spaced, series-connected catalyst beds 21. Each bed 21 also receives the dilute ethylene feed 17 such that the ethylene and the benzene-containing effluent from the guard bed 16 or the previous bed 21 pass cocurrently down through the bed. Again each bed 21 of the reactor 19 is typically operated at or near to 100% ethylene conversion.

The effluent from each bed 21, except for the bottom bed, of the reactor 19 is passed to a heat exchanger and flash drum, indicated collectively as 22, where the effluent is cooled and separated into a liquid stream 23 and a vapor stream 24. The liquid stream 23, which contains mostly benzene and ethylbenzene, is sent to the next catalyst bed in the reactor 19. The vapor stream 24 normally contains mostly ethane but, in view of its volatility, can contain from about 10 to about 90% benzene which must be removed before the ethane can be used as, for example, a fuel source. The stream 24 is therefore passed to a prefractionator 25, where most of the benzene condenses, and then to a scrubber 26, where the remainder of the benzene is adsorbed by streams heavier than ethylbenzene, for example, the polyethylated benzenes or residue produced in the process.

The effluent 20 from the bottom bed of the reactor 19, which contains the desired ethylbenzene product as well as unreacted benzene and small quantities of polyethylated benzenes and ethane, is fed initially to the prefractionator 25 where the ethane is removed as overhead and passed to the scrubber 26. The bottoms fraction from the prefractionator 25 is passed to a benzene column 27 where the unreacted benzene is removed as overhead and recycled to the reservoir 14. The bottoms fraction from the benzene tower is passed to an ethylbenzene column 28 where the desired ethylbenzene is recovered as overhead and the bottoms fraction is passed to a PEB column 29. The polyethylated benzenes, mostly diethylbenzene, are removed as an overheads fraction from the PEB column 29. The bottoms fraction from PEB column 29 is removed as residue. Preferably, at least a portion of the polyethylated benzenes or residue may be passed through the scrubber 26 before being fed to a transalkylator 31. The transalkylator 31 also receives a supply of benzene from the reservoir 14 and is operated under conditions such that 20–80% of the polyethylated benzenes are converted to ethylbenzene. The effluent 32 from the transalkylator is combined with the effluent 20 from the reactor 19 as it passes to the prefractionator 25 and then the columns 27, 28 and 29.

The invention will now be more particularly described with reference to the following Example.

EXAMPLE

The first and fourth beds of a four-bed ethylbenzene reactor were simulated in an adiabatic fixed-bed laboratory flow reactor with a four-gram catalyst loading of an appropriate zeolite to facilitate the alkylation of benzene with ethylene.

The first bed liquid feed was pure benzene, whereas the simulated fourth bed liquid feed had the following composition:

| | |
|---|---|
| Benzene | 77.80% |
| Ethylbenzene | 20.86% |
| Diethylbenzene | 1.18% |
| Triethylbenzene | 0.04% |

The simulated first bed gas feed was a mixture of ethylene and ethane at a molar ratio 65:35. Simulated operation of the first bed was at a temperature of 200° C., a pressure of 350 psig (2514 kPa), a WHSV of 0.68 (ethylene basis) and an aromatic:ethylene ratio of 57:1 weight basis). The ethylene conversion was 98.0%.

In one simulation, without interstage ethane removal, the simulated fourth bed gas feed was a mixture of ethylene and ethane at a molar ratio 33:67. Simulated operation of the fourth bed was under the same conditions as the first bed and the ethylene conversion was only 88.0%.

In another simulation, with interstage ethane removal, the simulated fourth bed gas feed was a mixture of ethylene and ethane at a molar ratio 67:33. Simulated operation of the fourth bed was again under the same conditions as the first bed but now the ethylene conversion had increased to 99.5%.

What is claimed is:

1. A process for producing an alkylaromatic compound by reacting an alkylatable aromatic compound with a feed comprising an alkene and an alkane in a multistage reaction system comprising a plurality of series-connected alkylation reaction zones each containing an alkylation catalyst, the process comprising the steps of:
   (a) operating at least one of said alkylation reaction zones under conditions of temperature and pressure effective to cause alkylation of said aromatic compound with said alkene in the presence of said alkylation catalyst, said temperature and pressure being such that part of said aromatic compound is in the vapor phase and part is in the liquid phase;
   (b) withdrawing from said one alkylation reaction zone an effluent comprising said alkylaromatic compound, unreacted alkylatable aromatic compound, any unreacted alkene and said alkane;
   (c) removing at least part of said alkane from said one alkylation reaction zone effluent to produce an alkane-depleted effluent; and
   (d) supplying said alkane-depleted effluent to another of said alkylation reaction zones.

2. The process of claim 1 wherein said feed comprises at least 20 wt % of said alkene.

3. The process of claim 1 wherein said feed comprises about 20 to about 80 wt % of said alkene.

4. The process of claim 1 wherein said alkane has the same number of carbon atoms as said alkene.

5. The process of claim 1 wherein said alkylatable aromatic compound includes benzene.

6. The process of claim 1 wherein said alkene includes ethylene and said alkane includes ethane.

7. The process of claim 5 wherein said alkene includes ethylene and said alkylaromatic compound includes ethylbenzene.

8. The process of claim 7 wherein said conditions in step (a) include a temperature of 150 to 270° C. and a pressure of 675 to 8300 kPa.

9. The process of claim 7 wherein said conditions in step (a) include a temperature of 170 to 220° C. and a pressure of 1500 to 4000 kPa.

10. The process of claim 1 wherein alkylation catalyst includes a molecular sieve selected from the group consisting of MCM-22, PSH-3, SSZ-25, ERB-1, ITQ-1, ITQ-2, MCM-36, MCM-49 and MCM-56.

11. The process of claim 1 wherein alkylation catalyst includes a molecular sieve having a Constraint Index of about 2 to about 12.

12. The process of claim 11 wherein alkylation catalyst includes a molecular sieve selected from the group consisting of ZSM-5, ZSM-11, ZSM-12, ZSM-22, ZSM-23, ZSM-35, and ZSM-48.

13. The process of claim 1 wherein alkylation catalyst includes a molecular sieve having a Constraint Index of less than 2.

14. The process of claim 13 wherein alkylation catalyst includes a molecular sieve selected from the group consisting of zeolite beta, zeolite Y, Ultrastable Y (USY), Dealuminized Y (Deal Y), mordenite, ZSM-3, ZSM-4, ZSM-18, and ZSM-20.

15. The process of claim 1 wherein said removing step (c) includes passing said one alkylation reaction zone through a flash drum.

16. The process of claim 1 comprising the additional steps of:
   (i) separating a polyalkylated aromatic fraction from an effluent of a final alkylation reaction zone, and
   iii) contacting at least part of said polyalkylated aromatic fraction with a transalkylatable aromatic compound in the presence of a transalkylation catalyst under transalkylating conditions.

17. The process of claim 16 including the further step of contacting said alkane removed in step (c) with at least part of said polyalkylated aromatic fraction such that said polyalkylated aromatic fraction adsorbs unreacted aromatic compound contained by said alkane.

18. The process of claim 1 comprising the further step of contacting said alkylatable aromatic compound and said feed with an alkylation catalyst in a by-passable prereactor separate from and upstream of said multistage reaction system.

19. The process of claim 1 comprising the further step of contacting unreacted alkylatable aromatic compound and unreacted alkene from said multistage reaction system under alkylation conditions with an alkylation catalyst in a finishing reactor separate from and downstream of said multistage reaction system.

* * * * *